(12) United States Patent
Klepper

(10) Patent No.: US 6,460,540 B1
(45) Date of Patent: Oct. 8, 2002

(54) ENDOTRACHEAL TUBE SUMP

(76) Inventor: Mark S. Klepper, 6 Wren Valley Cove, Austin, TX (US) 78746

( * ) Notice: Subject to any disclaimer, the term of this patent is extended or adjusted under 35 U.S.C. 154(b) by 0 days.

(21) Appl. No.: 09/542,398

(22) Filed: Apr. 4, 2000

Related U.S. Application Data

(60) Provisional application No. 60/127,716, filed on Apr. 5, 1999.

(51) Int. Cl.$^7$ ............................................. A61M 16/00

(52) U.S. Cl. ............................. 128/207.14; 128/207.15

(58) Field of Search ....................... 128/207.14–207.18, 128/911, 912, 200.24, 200.26, 201.26, 203.12, 205.19

(56) References Cited

U.S. PATENT DOCUMENTS

| | | | | |
|---|---|---|---|---|
| 4,231,365 A | * | 11/1980 | Scarberry | 128/207.15 |
| 4,840,173 A | * | 6/1989 | Porter, III | 128/207.15 |
| 5,009,227 A | * | 4/1991 | Nieuwstad | 128/200.26 |
| 5,038,766 A | * | 8/1991 | Parker | 128/200.26 |
| 5,067,497 A | * | 11/1991 | Greear et al. | 128/207.15 |
| 5,241,956 A | * | 9/1993 | Brain | 128/207.15 |
| 5,372,131 A | * | 12/1994 | Heinen, Jr. | 128/207.15 |
| 5,513,627 A | * | 5/1996 | Flam | 128/200.26 |
| 5,520,175 A | * | 5/1996 | Fry | 128/207.15 |
| 5,588,424 A | * | 12/1996 | Insler et al. | 128/207.15 |
| 5,819,723 A | * | 10/1998 | Joseph | 128/207.14 |
| 5,964,217 A | * | 10/1999 | Christopher | 128/200.26 |
| 6,062,223 A | * | 5/2000 | Palazzo et al. | 128/207.15 |
| 6,142,144 A | * | 11/2000 | Pacey | 128/200.26 |

OTHER PUBLICATIONS

Hospital–acquired Pneumonia in Adults; Am.J.Resp.Crit.Med., vol. 153, pp. 1711–1725, 1995.

Microbiology & Epidemiology of Hospital–Acquired Pneumonia, AFC I, (Supplement 2)pp. 11–18; Influence of Airway Management on Ventilator–Associated Pneumonia, JAMA Mar. 11, 1998 vol. 279, No. 10 pp. 781–787.

Continuous Aspiration of Subglottic Secretions in Preventing Ventilator–Associated Pneumonia, American College of Physicians, 1995, pp. 179–186.

Prevention of nosocomial pneumonia in intubated patients:respective role of mechanical subglottic secretions drainage and stress ulcer prophylaxis; Intensive Care Medicine 1992, vol. 18 pp. 20–25.

Wound Disinfection with ultraviolet radiation, Journal of Hospital Infection 1995, pp. 85–93.

Fans, Filters, or Rays? Pros and Cons of the Current Environmental Tuberculosis Control Technologies; Infection Control and Hospital Epidemiology, vol. 14, No. 12 pp. 681–685.

UV–Flash: Clinical Evaluation in 97 Patients; Results of a French Multicenter Trial, Short Reports, pp. 86–89.

Reduced Risk for Peritonitis in CAPD with Use of a UV Connector Box, Peritoneal Dialysis International vol. 11, 1991 pp. 128–130.

The Use of Germidical Lamps to Control Tuberculosis in Healthcare Facilities, Infection Control and Hospital Epidemiology, Dec. 1993, pp. 723–728.

*Primary Examiner*—Glenn K. Dawson
*Assistant Examiner*—Teena Mitchell
(74) *Attorney, Agent, or Firm*—Paul M Denk

(57) ABSTRACT

A sump assembly having a tubular body with a drain at the distal end for use with an endotracheal tube which provides for the removal of the secretions around and near the endotracheal tube cuff, while the endotracheal tube remains in the nasal or throat passages of the patient.

15 Claims, 6 Drawing Sheets

OTHER PUBLICATIONS

Sterilization and Disinfection, Chapter 3, Growth & Death of Bacteria, pp. 59–60.

Sterilization and Disinfection; Growth and Death of Bacteria.

Pierre–Yves Durand et al: UV–Flash: Clinical Evaluation in 97 Patients; Results of a French Multicenter Trial.

Bernd G. Stegmayr: Reduced Risk for Peritonitis in CAPD with the Use of a UV Connector Box, 1991.

Ph. Mahul et al: Prevention of nosocomial pneumonia in intubated patients, Mar. 1, 1991.

Janet M. Macher: The Use of Germicidal Lamps to Control Tuberculosis in Healthcare Facilities, Dec. 1993.

Edward A. Nardell: Fans, Filters, or Rays? Pros and Cons of the Current Environmental Tuberculosis Control Technologies, Dec. 1993.

G. J. S. Taylor et al: Wound infection with ultraviolet radiation, Jan. 20, 1995.

Jordi Valles et al: Continuous Aspiration of Subglottic Secretions in Preventing Ventilator–Associated Pneumonia, Feb. 1, 1995.

American Thoracic Society: Hospital–acquired Pneumonia in Adults, Nov. 1995.

Kathleen Steger et al: Microbiology and Epidemiology of Hospital–Acquired Pneumonia, 1997.

Deborah Cook et al: Influence of Airway Management on Ventilator–Associated Pneumonia, Mar. 11, 1998.

\* cited by examiner

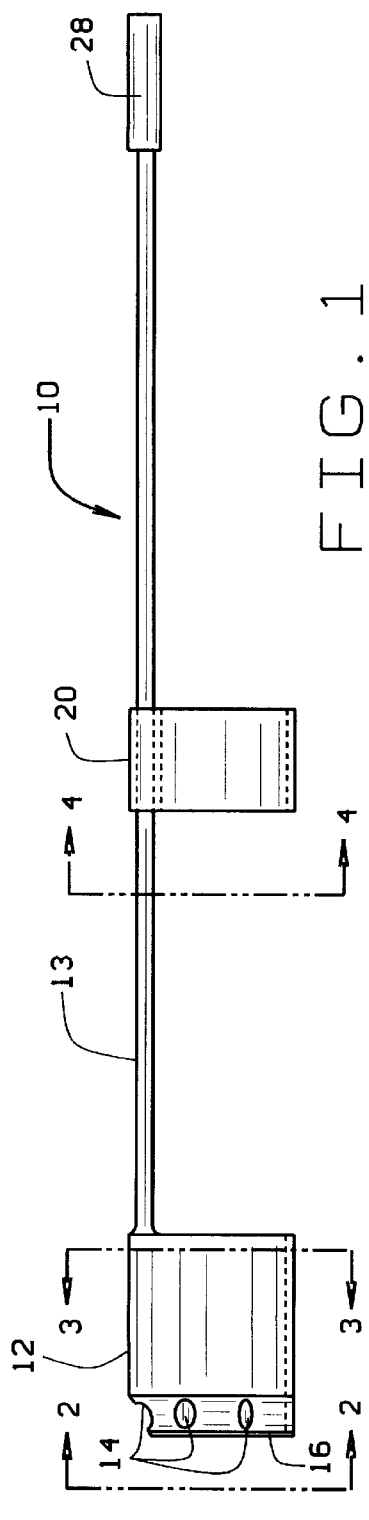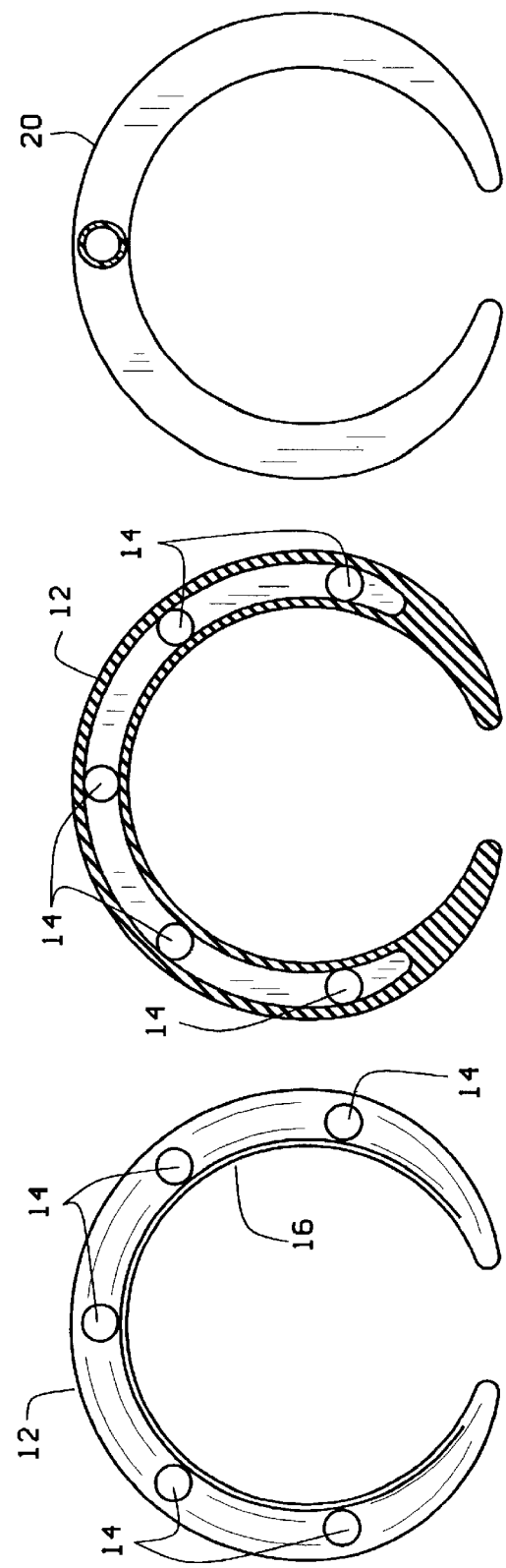

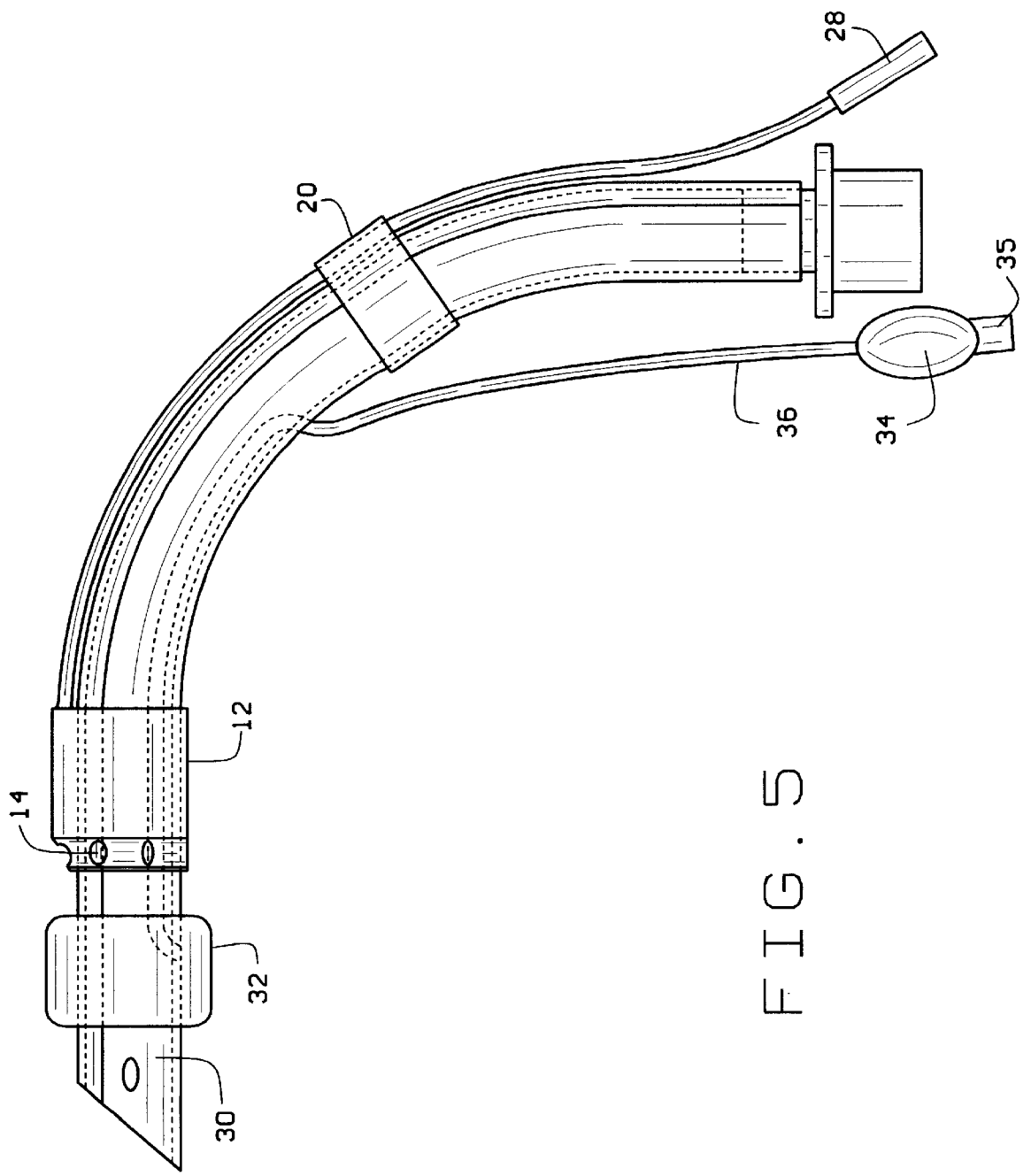

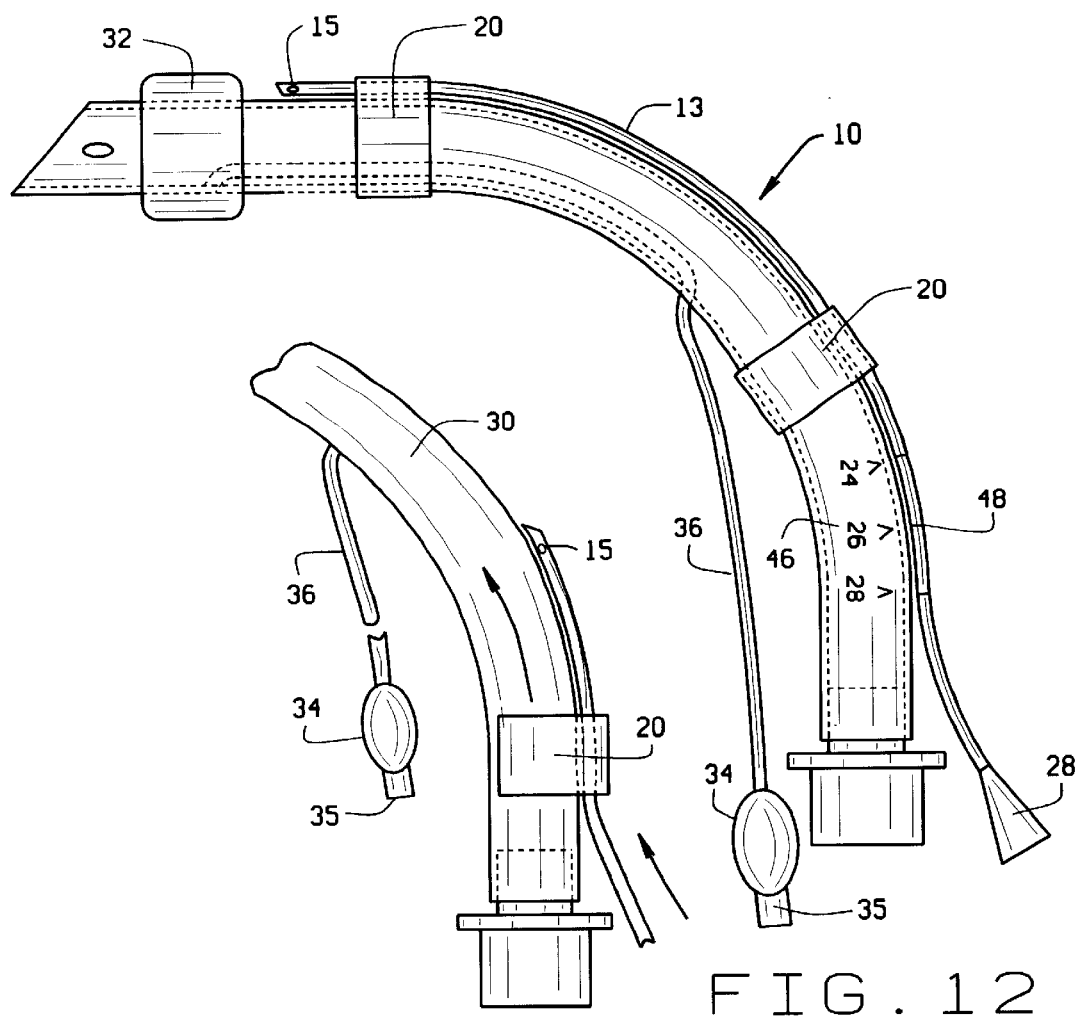
FIG. 11
FIG. 12
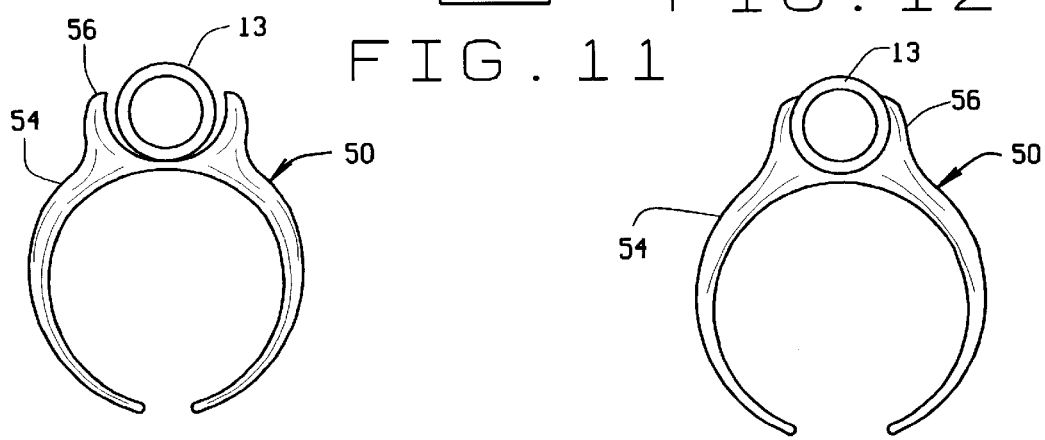
FIG. 13A
FIG. 13B

ENDOTRACHEAL TUBE SUMP

CROSS-REFERENCE TO RELATED APPLICATIONS

This application claims priority to provisional applications Serial No. 60/127,716, filed Apr. 5, 1999.

BACKGROUND OF THE INVENTION

In certain instances of accident or illness, it is necessary to perform intubation of the trachea in order to allow continued breathing by a patient. Such a process was first described in the late 1800's. The trachea was intubated via the mouth utilizing a short metal tube for purposes of resuscitation and positive pressure ventilation. Since that time the endotracheal tube has evolved to a disposable flexible plastic tube of varying diameters and lengths used in newborns, children and adults.

In the case of the larger endotracheal tubes, a low pressure, high volume, thinwalled, rubberized cuff is inflated with air using a small separate line and valve system. This allows the cuff to create a seal between the endotracheal tube at its distal portion and the trachea of the patient. The proximal portion of the tube projecting from the mouth or nose of the patient allows connection to standard ventilating devices.

Endotracheal tubes also are temporarily used for inhaling general anesthesia or establishment of an artificial airway or for purposes of ventilatory support. In some instances, the endotracheal tube may remain in place for up to two or three weeks or longer. Complications arising from endotracheal intubation of the trachea are development of tracheitis, bronchitis, or pneumonia. What is known to the medical profession, is that various types of illnesses related to the trachea tube, and the fluid accumulations that may occur, frequently lead to illnesses, and their complications, which can have serious results. Studies have revealed secretions around the endotracheal tube cuff tend to pool in the space above the cuff as well as in the posterior oropharynx. These secretions arise from the mouth, nose, sinuses, gastroesophageal secretions and products of enteral feeding.

Furthermore, gastric reflux and accumulation of oral/nasal secretions during surgery can result in aspiration while the patient is intubated during surgery, particularly in high risk operative procedures. High risk patients are those who undergo emergency surgery, like in trauma or obstetric cases, long operations (four hours or more), upperD.N. abdominal surgeries requiring manipulation of the stomach or patients with known hiatal hernia or severe gastroesophageal reflux disease. The precise incidence is unknown since it often occurs in an occult fashion and only is implicated retrospectively when the postoperative patient develops pneumonia or respiratory failure six to twenty-four hours after surgery.

A safe, effective and reliable means for evacuating these secretions from above the endotracheal tube cuff would most generally reduce the severity and/or frequency of ventilator associated pneumonia and other diseases.

SUMMARY OF THE INVENTION

It is one object of the invention to provide an apparatus and method for the safe, effective and reliable means for evacuating these secretions from above the endotracheal tube cuff.

Another object of the invention is to provide such an apparatus that can be introduced into the patient adjacent a prepositioned endotracheal tube.

Another object of the invention is to provide such an apparatus that can be introduced into the patient adjacent a prepositioned endotracheal tube by using preattached clips that can slidingly engage the prepositioned endotracheal tube.

Still another object of the invention is to provide such an apparatus that can be introduced into the patient attached to and along side the endotracheal tube.

The present invention provides a sump assembly which allows removal of the secretions around and near the endotracheal tube cuff, while the endotracheal tube remains in the nasal or throat passages of the patient. Such secretions are typically located in the pharynx, supraglottic region, infraglottic region, and trachea region. The endotracheal tube sump of the present invention reduces the pooling of secretions by removal thereof, thus preventing pneumonia, bronchitis and other related diseases. The sump fits partially around the tracheal tube and when being installed or removed follows the path of the endotracheal tube down to the endotracheal tube cuff.

The endotracheal tube sump includes a tubular body with a distal end and a proximal end. The distal end includes a drain which can be formed as part of the tubular body or formed of flexible, or perhaps even semi-rigid, e.g. formed of a polymer, or other appropriate material, and even in certain instances rubber containing silicone. This drain contains at least one port, or perhaps several ports, through which secretions enter into the tubular body to be removed through the proximal end by a suction means. Located at or near the distal end is a guide affiliated with the drain. Another guide, ring or partial annulus, identified as a proximal guide can be positioned at the proximal end of the tubular body. Depending on the length of the tubular body, one or more proximal guide may be provided. The guide is comprised of an open ring of flexible material and is sized to easily fit around the endotracheal tube. Hence the sump is slidably inserted into the patient, and follows the path of the endotracheal tube.

Beyond the last proximal guide, is attached a connecting fitting to a suction catheter. The fitting provides attachment of the sump assembly to an external suction means or vacuum source or other appropriate attachment, including syringe fittings, stop cocks and other devices intended to irrigate or provide installation of other materials.

BRIEF DESCRIPTION OF THE DRAWINGS

FIG. 1 is a side elevational view of one embodiment of the invention;

FIG. 2 is a front elevational view taken along line 2—2;

FIG. 3 is an cross sectional view taken along line 3—3;

FIG. 4 is a front elevational view taken along line 4—4;

FIG. 5 is a side elevational view of one embodiment of the invention when installed on an endotracheal tube;

FIG. 11 is a side elevational view of a sump assembly of the present invention being installed on an endotracheal tube;

FIG. 12 is a side elevational view thereof with the sump assembly fully installed;

FIG. 13A is an enlarged end plan view of an alternative embodiment of a sump assembly guide of the present invention in an open position for seating a tubing; and FIG. 13B shows the guide of FIG. 13A in a closed position with the tubing seated in the cradle.

DETAILED DESCRIPTION OF THE INVENTION

Figures 6, 7:
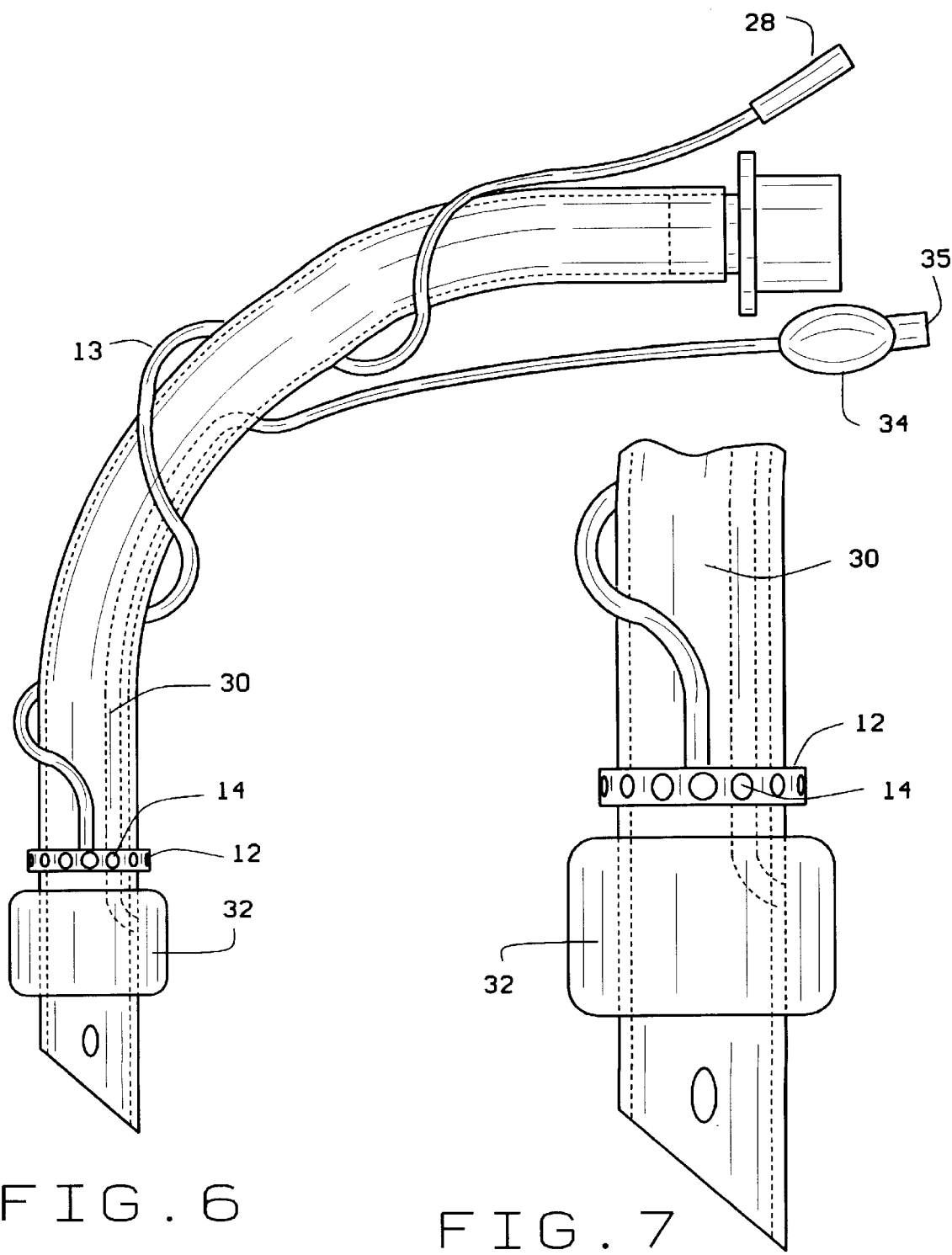
FIG. 6 is a side elevational view of an sump assembly of this invention with the spiral configured tubular body being shown spiraling around the endotracheal tube for threading, by turning, downwardly towards the endotracheal cuff.
FIG. 7 discloses a view of the lower end of the sump assembly, as it is turned in a threading like manner, and reaches its proximity above the cuff to function to evacuate secretions accumulated at that location within the trachea.

FIG. 1 depicts a sump assembly of the present invention indicated generally by reference numeral 10. Sump assembly 10 includes distal suction means or drain 12, a front elevational view of which is shown in FIG. 2, fluidly connected to an elongated, tubular body or suction tube 13. The drain 12 allows for suctioning or irrigation at the distal end of the sump assembly. The drain 12 has one or more ports 14 for entry of the secretions and fluids, and the number of ports employed, and formed into the distal end of the suction means, depends upon the degree of suction of vacuum means required in order to remove secretions of a select viscosity from its accumulation at the vicinity of the inward end of the previously employed and inserted endotracheal tube. The ports 14 in the drain permit entry of unwanted secretions into the drain 12 whereupon the secretions are removed via vacuum to a disposal receptacle.

In addition, the drain 12 has a radiopaque mark 16 to indicate its inserted location. The radiopaque mark 16 allows for positioning the distal suction means appropriately with respect to the endotracheal tube 30 (FIG. 5) already installed. The drain 12 is generally in the form of a ring open at the bottom to permit fitting around the endotracheal tube (See FIGS. 2 and 3). The drain 12, may undertake any related shape, such as that as shown in FIGS. 1, 5, 6 or may even comprised openings 15 (See, FIGS. 8 and 12) formed in the distal end of the tubular body 13. Thus, the shape of drain 12 is not necessarily critical to its functionality, but has to have sufficient structure. However, if the drain 12 also functions as a guide ring, as shown in FIGS. 1 and 5, for example, it must be configured so as to allow for its slide along the endotracheal tube 30 tube, during its insertion, or removal, and to locate proximate the lower end of the endotracheal tube, and just above its inflated cuff 32, so as to provide means for removal of the secretions accumulated at that location, and to minimize the risk of generating complications or infections, as previously explained. As a guide ring, the drain 12 generally is configured as a clip, as shown in FIG. 2.

The assembly may include one or more additional guide rings 20, also configured like clips, positioned along the length of the tube 13 in a spaced apart relationship, to facilitate insertion and removal as will be explained below.

The relationship of the drain 12 of the present invention and the endotracheal tube 30 is depicted in FIG. 5 where the drain 12 approaches the position of the cuff 32 of the endotracheal tube. When the endotracheal tube 30 is installed in the patient, the cuff 32 is inflated to provide a snug, secure fit. The cuff 32 is inflated by injecting air into the cuff by bulb 34 which retains the injected air by means of a valve 35 so as to cause the inflation of said cuff, and to prevent the secretions generated above the cuff 32 from permeating downwardly, and into the trachea, and to prevent its localizing therebelow and causing the type of infection as previously described. The bulb 34 may be formed as a pump, having resiliency to it, and by squeezing of the same, sucking air into the bulb and forcing it downwardly through the tubing 36, to inflate the associated cuff 32.

Obviously, the valve also allows for deflation of the cuff, when operated to achieve this result. But, because the cuff, when inflated, acts as a barrier against downward migration of such secretions, they accumulate above the cuff, and the purpose of this current invention is to provide means for evacuating those secretions before they cause deleterious problems to the patient, because of their presence.

At the proximal end of the tube 13 is a connecting fitting 28. The connecting fitting 28 can be connected to a vacuum source, such as a powered vacuum pump, a syringe or the like, or other suitable attachments. Furthermore, the suction can be discontinued and materials, such as antibiotics or other medications, can be introduced into the fitting with a syringe, flow through the tube 13 to be instilled in the patient through the ports 14 in the drain 12.

The subject matter of this invention is to provide for a clamping of the sump assembly 10 onto the endotracheal tube 30, as shown, and then sliding it by means of its guides whether the guides be a drain 12, or only guide rings 20, downwardly upon the previously implanted endotracheal tube, until it locates at the position desired. Furthermore, in order to facilitate such manipulation, it is likely that lubricating means may be provided internally of the drain 12, and the guide ring 20, either in the form of some type of lubrication, which may be manually placed thereon, in order to reduce any friction generated between these components and the endotracheal tube. Or, the tube 13 may be a compound tube, and have a separate channel that extends downwardly through the guide ring 20, and into the drain 12 to dispense a small amount of lubricant thereon, during insertion and withdrawal of the assembly, in order to facilitate its application. Or, even a separate tube, such as that similar to what is shown at 13, may be applied to the guide ring 20, and the drain 12, to add lubrication in the manner as previously described.

This device may also be utilized for delivery other materials, as stated above, such as irrigants, antibiotics, or other solutions into the vicinity of the lower end of the inserted endotracheal tube. Additionally, diagnostic sampling of secretions may be performed, in order to provide for their testing, to determine the extent of any bacterial or other contamination, and the type of infection that may be generated at the vicinity of the cuff 32, so that proper treatment may be prescribed.

As can be seen in FIGS. 6 and 7 of the drawings, the endotracheal tube 30, with its previously located cuff 32, and having its air tube 36 attached thereto, will have been emplaced into the trachea and downwardly into the vicinity of its final location. In an alternative embodiment the tubular body or tube 13, is preformed into a spiraling configuration, as can be noted, and can be applied to the endotracheal tube 30, by turning or rotating, in a manner of threading to provide for its shifting downwardly upon the endotracheal tube 30, as it is turned, in a spiral fashion, to attain a locating of drain 12 just proximately above the cuff 32, and once it achieves this location, its intake ports 14 will allow for evacuation of secretions accumulated at that location, just above the cuff, to attain the results as explained for this invention. This is just an alternative or modification to the concept of this invention, which is to use a tubing, which may be turned in a screwlike motion, to thread it onto the tubing 30, until such as it achieves a locating as disclosed in FIG. 7. Thus, the spirally configured tube 13 will function as a guide, for the sump assembly, to provide for its subsequent locating downwardly within the trachea, in order to provide for the evacuation of the accumulation of fluids at that location, and hopefully a minimization of the generation of any infections, at that location.

Figure 8:
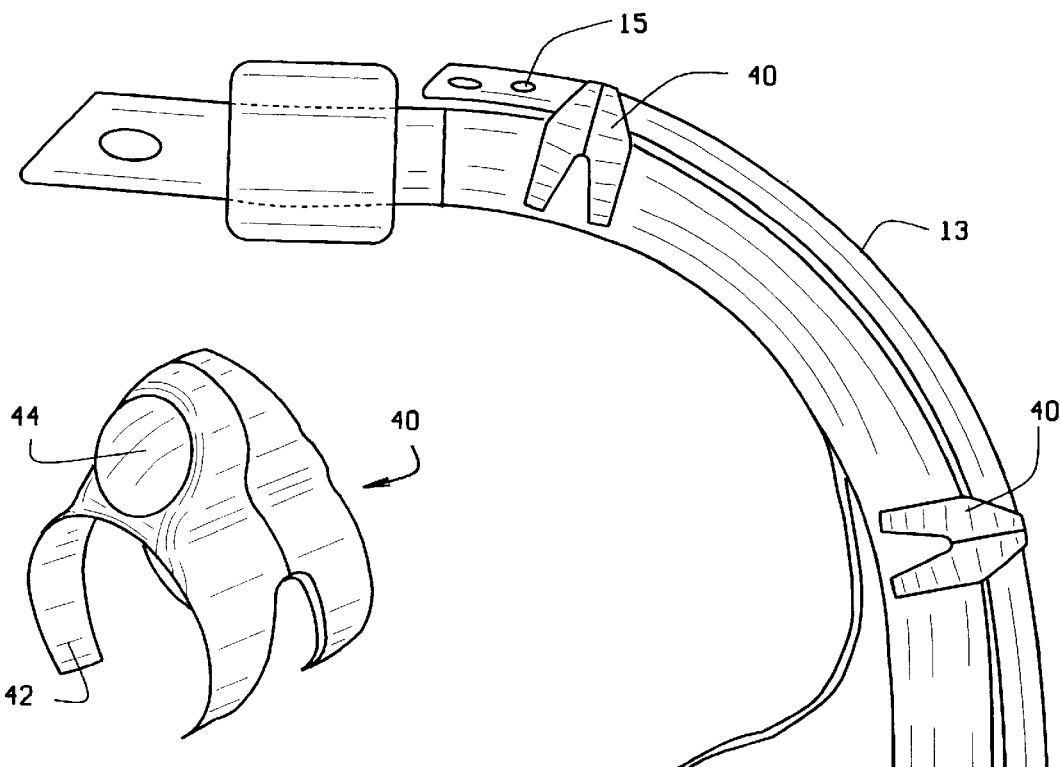
FIG. 8 is a side elevational view of another embodiment of the invention when installed on an endotracheal tube.
Figure 10A:
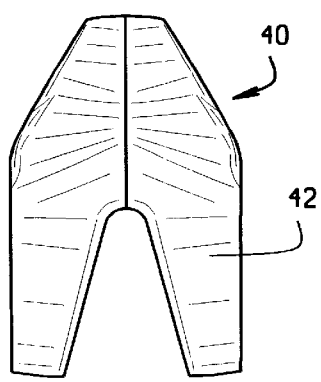
FIG. 10A is an enlarged perspective view of an alternative embodiment of a sump assembly clip of the present invention.
Figure 10D:
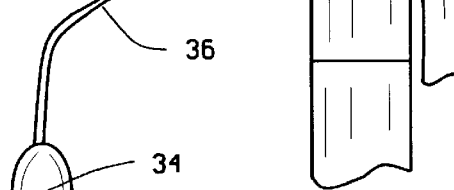
FIG. 10D is a side elevational view thereof.
Figure 10C:
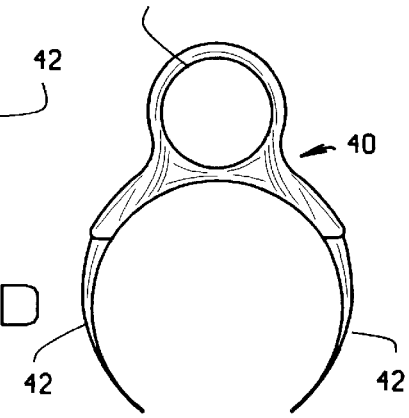
FIG. 10C is an end plan view thereof.
Figure 10B:
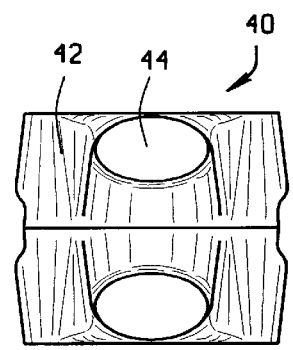
FIG. 10B is a top plan view thereof.

FIG. 8 illustrates another embodiment of the sump assembly of the present invention, particularly the guides 40. As can be seen, the embodiment of the invention shown in FIG. 8 does not have a separate drain structure but includes drain openings 15 formed in the distal end of tube 13. Since there is no separate drain structure to function as a guide, this sump assembly includes a guide 40 at the distal end, proximate the openings 15. Furthermore, additional guides 40 are spaced toward the proximal end. The guides 40 are shown in greater detail in FIGS. 10A–10D and include a semicircular clip section 42 and a circular tube channel 44 formed like a boss at the tip of the clip. The tube 13 is positioned in the tube channel 44 and can be secured there in by ultrasonic welding or other appropriate means. The sump assembly illustrated in FIG. 8 is installed on the endotracheal tube in the same manner as other embodiments.

Figure 9:
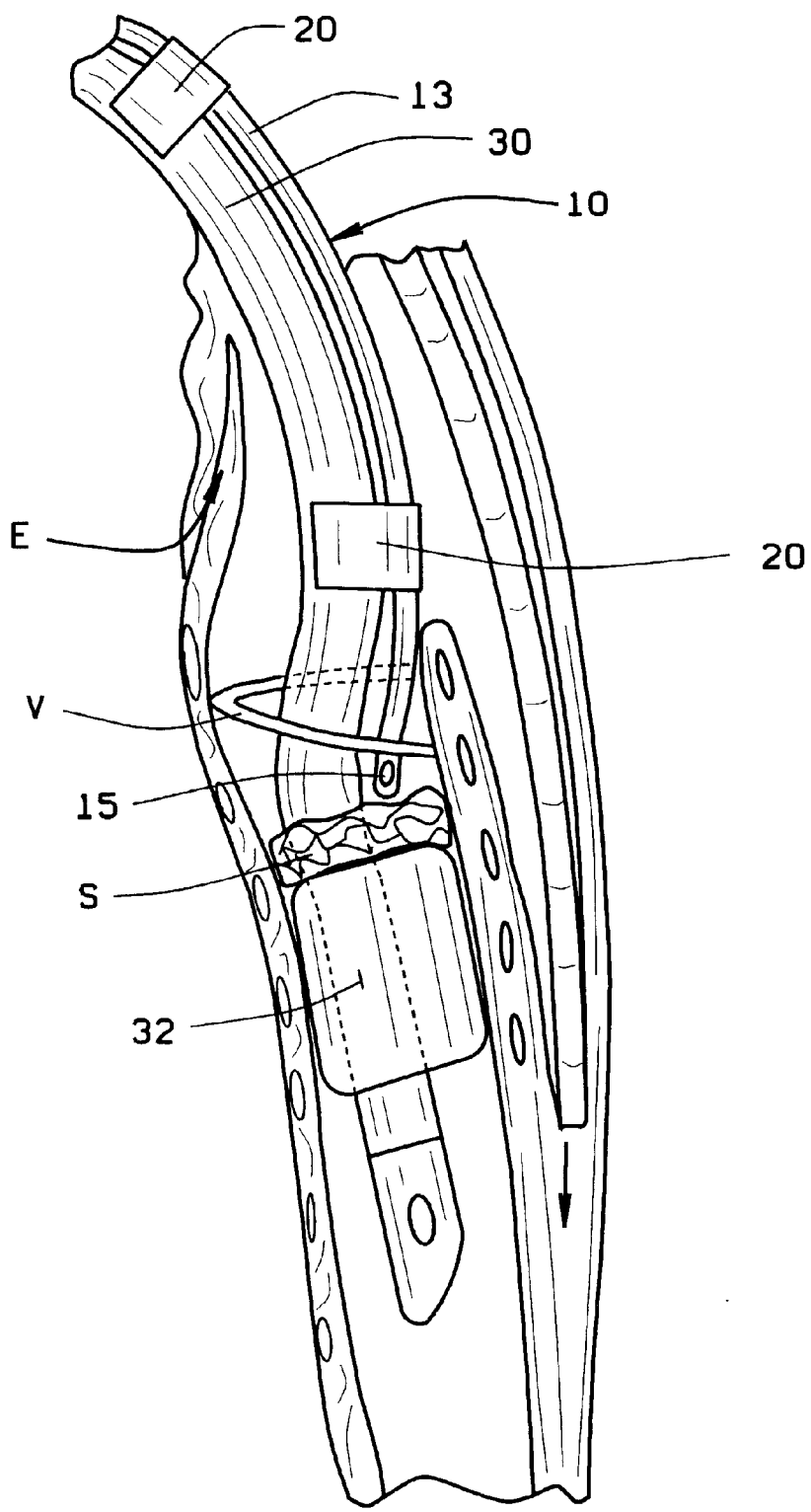
FIG. 9 is a side elevational view of another embodiment of the invention when installed on an endotracheal tube and inserted in a patient.

FIG. 9 illustrates a representative embodiment of a sump assembly 10 of the present invention placed in a patient along with an endotracheal tube. For reference, the physiological structures of the patient will be referenced as landmarks and include the epiglottis E, the vocal cords V and the accumulated secretions S above the cuff 32 of the endotracheal tube 30. As will be appreciated, the sump assembly 10 of the present invention is optimally placed adjacent the endotracheal tube 30 with a drain opening 15 accessible by the secretions S when suction is applied through the tube 13.

FIGS. 11 and 12 better illustrate the installation of a sump assembly 10 of the present invention adjacent an endotracheal tube 30. As shown, the distally positioned guide 20 is placed over the proximal end of the endotracheal tube 30. The assembly is urged down the endotracheal tube with the guide 20 keeping it adjacent the tube. As the sump assembly moves down the length of the endotracheal tube, subsequent guides 20 are attached to the endotracheal tube, as shown in FIG. 12. The endotracheal tube 30 illustrated in FIG. 12 includes indexing marks 46 which can be aligned with indexing marks 48 on the sump tube 13. Alignment of the appropriate indexing marks aid in the proper positioning of the drain opening 15 with respect to the cuff 32.

FIGS. 13A and 13B illustrate another alternative embodiment of guide. It will be noted that guide 50 includes a clip 54 and a tubing cradle 56. The guide 50 is constructed from a resilient material, such as plastic. By applying pressure such as squeezing the legs 58 of the clip 54, the cradle 56 opens for the insertion of the tubing 13. Release of the legs 58 of the clip allows the cradle to close and secure the tube 13 therein.

Variations or modifications to the subject matter of this invention may occur to those skilled in the art upon review of the summary herein, and upon undertaking a study of the description of its preferred embodiment. Such variations may be within the scope of this invention.

What is claimed is:

1. A sump assembly for coadministration with an endotracheal tube for the removal of secretions adjacent the endotracheal tube; the sump assembly comprising a vacuum tube having a port at one end and being adapted at a second end for connection to a suction device; at least one guide for attachment to the endotracheal tube to facilitate placement of the sump assembly adjacent the endotracheal tube; said guide having a length substantially shorter than the length of the vacuum tube; wherein the at least one guide for attachment to the endotracheal tube to facilitate placement of the sump adjacent the endotracheal tube has a plurality of drain openings formed therein, said port comprising said drain openings in said guide.

2. The sump assembly of claim 1 wherein said at least one guide for attachment to the endotracheal tube comprises an at least a first guide having the plurality of drain openings, and a second guide, said guides both having a length substantially shorter than the length of the vacuum tube, and being spaced apart along the vacuum tube.

3. The sump assembly of claim 1 and further comprising a fitting at said second end of said vacuum tube.

4. The sump assembly of claim 3 wherein said fitting is for the attachment of said suction device.

5. The sump of claim 4 wherein said fitting is for the introduction of material through the sump assembly.

6. The sump assembly of claim 1 wherein said at least one guide comprises a clip; said clip comprising a retaining portion which receives said vacuum tube and an engaging portion which is sized and shaped to engage the endotracheal tube.

7. The sump assembly of claim 6 wherein said clip engaging portion is generally C-shaped.

8. The sump assembly of claim 6 wherein said clip retaining portion defines a tubular passage.

9. The sump assembly of claim 6 wherein said clip retaining portion is generally C-shaped, and is sized and shaped to receive and grip said vacuum tube.

10. A sump assembly for coadministration with a endotracheal tube for the removal of secretions adjacent the endotracheal tube; said sump assembly comprising an elongated tubular body having a preformed spiral configuration for rotational application around the endotracheal tube.

11. In combination, an endotracheal tube and a sump:
said endotracheal tube comprising a proximal end, a distal end and a securing cuff adjacent the distal end of said endotracheal tube;
said sump comprising a suction tube having a distal end and a proximal end; means for positioning the suction tube adjacent the endotracheal tube, a drain at the distal end of said suction tube positioned adjacent the securing cuff of the endotracheal tube, and a fitting at the proximal end of the suction tube for the attachment of a suction device; said suction tube comprising a tubular body portion preconfigured in a spiral configuration.

12. The combination of claim 11 wherein the means for positioning the suction tube adjacent the endotracheal tube comprises at least one guide; said guide slidedly engaging the endotracheal tube.

13. The combination of claim 11 wherein the means for positioning the sump adjacent the endotracheal tube comprises a guide at the proximal end thereof, said guide including a port.

14. The combination of claims 11 wherein the means for positioning the sump adjacent the endotracheal tube comprises said tubular body portion pre-configured in a spiral configuration.

15. A method of removing secretions accumulated above a securing cuff located adjacent a distal end of an endotracheal tube inserted in a patient; the method comprising the steps of:

attaching a sump assembly to the endotracheal tube, said sump including an elongated tubular body having a proximal end and a distal end, means for attaching the sump to the endotracheal tube, a fitting at the proximal end of the elongated tubular body and a drain at the distal end of the elongated tubular body; the elongated tubular body of the sump being pre-configured in a spiral configuration whereby the tubular body is rotated about the endotracheal tube to attach the sump assembly to the endotracheal tube.

positioning the sump drain above the securing cuff of the endotracheal tube;

attaching a suction device to the fitting at the proximal end of the elongated tubular body; and actuating the suction device so as to draw secretions into the drain, through the tubular body and fitting and into the suction device.

* * * * *